United States Patent [19]

Webster et al.

[11] Patent Number: 5,005,410
[45] Date of Patent: Apr. 9, 1991

[54] HIGH TEMPERATURE HUMIDITY DETERMINING DEVICE AND PROCESS

[75] Inventors: Jeffrey Webster, Augusta; Stephen Richey; Robert Tuttup, both of Battle Creek, all of Mich.

[73] Assignee: Kellogg Company, Battle Creek, Mich.

[21] Appl. No.: 453,915

[22] Filed: Dec. 20, 1989

[51] Int. Cl.$^5$ .......................................... G01N 25/56
[52] U.S. Cl. .................................................. 73/335
[58] Field of Search .................. 73/335, 336, 336.5, 73/338

[56] References Cited

U.S. PATENT DOCUMENTS

| | | | |
|---|---|---|---|
| 2,643,464 | 6/1953 | Hadady | 34/48 |
| 3,265,301 | 8/1966 | Amdur et al. | 236/44 |
| 3,459,034 | 8/1969 | Kawaguchi . | |
| 3,603,135 | 9/1971 | Kawaguchi . | |
| 3,890,828 | 6/1975 | Pleva . | |
| 4,028,942 | 6/1977 | Gardiner | 73/335 |
| 4,221,058 | 9/1980 | Zagorzycki | 34/50 |
| 4,279,150 | 7/1981 | Land | 73/338 |
| 4,503,707 | 3/1985 | Rosa et al. | 73/336.5 |
| 4,507,875 | 4/1985 | Hirsch et al. | 34/44 |
| 4,559,823 | 12/1985 | Rosen et al. | 73/338 |

FOREIGN PATENT DOCUMENTS

2246371  3/1974 Fed. Rep. of Germany ..... 73/336.5

Primary Examiner—Jerry W. Myracle
Attorney, Agent, or Firm—Oblon, Spivak, McClelland, Maier & Neustadt

[57] ABSTRACT

A high temperature humidity determining device which measures the moisture content of gas streams with temperatures as high as, but not limited to 600° F. The device uses a solid state, thin film polymer type relative humidity/temperature sensor and electronic barometer to measure the properties of the gas stream. The unit does not require laboratory quality oxygen, ice water, distilled water or any other cleaning fluids. In order to avoid damage to the sensor, a sample is cooled to below about 300° F. prior to sampling. This is done by pumping the sample air through a thermostatically controlled sample conduit, and into a positively pressurized and thermostatically controlled sample chamber. A microprocessor calculates the humidity ratio and dew point of the sample or other moist air properties, and delivers data to a visual process indicator, as well as to any other desired output.

25 Claims, 8 Drawing Sheets

HIGH TEMPERATURE HUMIDITY DETERMINING DEVICE AND PROCESS

BACKGROUND OF THE INVENTION

Field of the Invention

The present invention is directed to an apparatus and process for determining the humidity of a high temperature gas sample. More particularly, the present invention is directed to a self contained and/or portable high temperature apparatus for determining the humidity of a hot gas sample without the need for an instrument quality oxygen source, distilled water source, ice water source or cleaning fluid. Gas samples with temperatures as high as, but not limited to 600° F., can be measured.

Description of the Background Art

It is often necessary to determine the humidity of a heated air stream. For example, in ovens or dryers it is desirable to monitor the humidity level of the cooking or drying air to achieve optimum cooking or drying levels. Sensors for determining the relative humidity of a low temperature gas are well known, for example Dunmore type Lithium Chloride (LiCl) cells. however, the relative humidity measured by such simple instruments without regard for the temperature of the air is not a good indicator of the quantity of water in the gas sample. Other low temperature devices that can be used to calculate more temperature independent moist air properties, such as "wet bulb/dry bulb" thermometers, are limited to temperatures well below 300° F.

More elaborate humidity sensors have been unsatisfactory for commercial use because they required specialized fluids such as instrument quality oxygen, distilled water or ice water which are not readily transportable and are best used in a controlled, i.e., laboratory, setting. An example of such a conventional humidity determining device may be found in U.S. Pat. No. 2,643,464 to Hadady, which requires a temperature equalizing bath. Other known devices are impractical in that they require additional cooling or cleaning fluids circulating therethrough.

More recently, there have been developed solid state moisture detectors which do not require cooling or cleaning fluids, or the use of instrument quality oxygen, distilled water or ice water. An example may be found in U.S. Pat. No. 4,503,707 to Rosa et al. which uses an aluminum oxide capacitive sensor. However, such solid state sensors do not have high temperature heat resistance capabilities. For example, the solid state thin film polymer type humidity/temperature sensor manufactured by the Rotronic Instrument Corporation can perform measurements in environments only up to 302° F. Higher temperatures will damage the thin film layers.

It is known from U.S. Pat. No. 4,221,058 to Zagorzycki to cool a hot gas sample before measuring the humidity of the sample in a sampling chamber. However, Zagorzycki is a simple drier control which uses a wet bulb type sensing element which requires saturation of a cloth with a salt solution. This introduces the problems associated with the conventional art such as that of Hadady, i.e., the need for special liquids which are not easily transported and applied in a controlled manner in practical settings. Additionally, the sample chamber in Zagorzycki is under negative pressure, which raises the possibility of inaccurate measurements due to air leaks into the sample chamber. Moreover, Zagorzycki is inherently incapable of being used in mass balance calculations which require determining a humidity ratio, since it does not sense the absolute air pressure, a parameter which must be known in determining the humidity ratio.

SUMMARY OF THE INVENTION

It is an object of the present invention to provide a high temperature humidity determining device which can measure the humidity of high temperature gas samples without the need for laboratory quality oxygen, distilled water, ice water or cleaning fluids.

It is another object of the present invention to provide a high temperature humidity determining process which can measure the humidity of high temperature gas samples without the need for laboratory quality oxygen, distilled water, ice water or cleaning fluids.

It is a further object of the present invention to provide a high temperature humidity determining device which is self contained and may be made portable.

The above, and other, objects are achieved according to the present invention by a high temperature humidity determining device having an insulated sample chamber which is supplied with a heated air sample by means for inducing the heated air sample from a region whose humidity is to be measured to flow into the insulated sample chamber. The inducing means includes a sample conduit connected to the region and having at least a cool down portion so that the heated air sample is cooled before reaching the insulated chamber. Heating means are provided for controlling the temperature of the heated air sample such that the heated air sample always remains above the dew point thereof in the insulated sample chamber and the inducing means. Sensing means are provided for sensing at least the temperature and relative humidity of the air sample in the sample chamber. Means are also provided for determining a humidity parameter of the air sample based upon at least the sensed temperature and relative humidity.

According to a further feature of the invention, the inducing means includes a pump connected to the sample conduit, with the head of the pump located in the sample chamber so that the pump head is heated and the sample chamber is positively pressurized by an air sample pumped by the pump.

According to a further feature of the invention, the sample conduit includes a flexible conduit portion connected between the more rigid cool down portion and the pump.

According to a further feature of the invention, the heating means comprises heating elements in both the flexible and rigid cool down insulated conduit portions, a conduit temperature sensor and an automatic control device comprising means for controlling actuation of the heating elements in the insulated conduit based upon the sensed temperature from the conduit temperature sensor.

According to a further feature of the invention, the heating means further comprises heating elements in the sample chamber, and a sample chamber temperature sensor. The automatic control device further comprises means for controlling actuation of the heating elements in the sample chamber based upon the sensed temperature from the sample chamber temperature sensor.

According to a further feature of the invention, the automatic control device comprises means having proportional, integral, and derivative (PID) control algorithms for maintaining the air sample at the set point temperature.

According to a further feature of the invention, the sensing means further comprise means for sensing the absolute air pressure in the sample chamber. The determining means comprise means for determining the humidity ratio and dew point temperature of the air sample based upon the sensed temperature, relative humidity and absolute pressure.

According to a further feature of the invention, the humidity parameter is the humidity ratio of the air sample. The determining means comprise a digital processor programmed to calculate the humidity ratio of the sampled air.

According to a further feature of the invention, the insulated chamber is formed from synthetic mica.

According to a further feature of the invention, the sample chamber has an air exhaust.

According to a further feature of the invention, the relative humidity and temperature sensors are together comprised by a thin film polymer type humidity sensor, and a resistive temperature device (RTD).

According to a further feature of the invention, an airtight quick disconnect connector is provided between the sample conduit and the pump head.

According to a further feature of the invention, humidity parameter display means are connected to the digital processor for displaying at least the calculated humidity ratio and dewpoint temperature.

According to a further feature of the invention, the insulated chamber, inducing means, heating means and determining means may be contained within a case so that the humidity determining device may be self contained and/or portable.

The above objects are also carried by a process for determining a humidity parameter of a heated air sample having a temperature greater than 300° F. The process comprises the steps of cooling the air sample to a temperature range above the dew point temperature of the sample and below about 300° F., maintaining the air sample temperature in that range, continuously flowing the air sample into an insulated sample chamber having positive air pressure, sensing at least the temperature and the relative humidity of the air sample maintained at that range, and calculating the humidity parameter based upon at least the sensed temperature and relative humidity.

According to a further feature of the invention, the temperature range is selected such that the sensed relative humidity is greater than 10%.

The above objects are also carried out according to the present invention by a portable and self contained high temperature humidity determining device which includes a case, an insulated sample chamber having an exhaust and being fixed in the case, a diaphragm type air pump fixed in the case and operatively connected to the sample chamber for pumping air into the sample chamber so that a flow of heated sample air in the sample chamber is positively pressurized. Thermostatically controlled heating elements are provided in the sample chamber for maintaining air in the sample chamber at a predetermined temperature. An airtight sample conduit has one end connected to the pump via a quick disconnect and another end connectable to a region whose humidity is to be measured. The heated air from the pump maintains the sample chamber at positive pressure. The sample conduit is insulated and heat traced so that the air sample may be controlled above dew point temperature but below the maximum operating temperature of relative humidity sensor. A thin film polymer type solid state relative humidity sensor and RTD are provided in the sample chamber. An absolute pressure sensor is also mounted to the chamber. A programmable computer is operatively connected to the sensors. The computer includes means for calculating at least the humidity ratio and the dew point of the air in the sample chamber based on signals from the sensors. An electronic display means is operatively connected to the computer for displaying at least the calculated dew point and humidity ratio.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENT

Figures 1, 2:
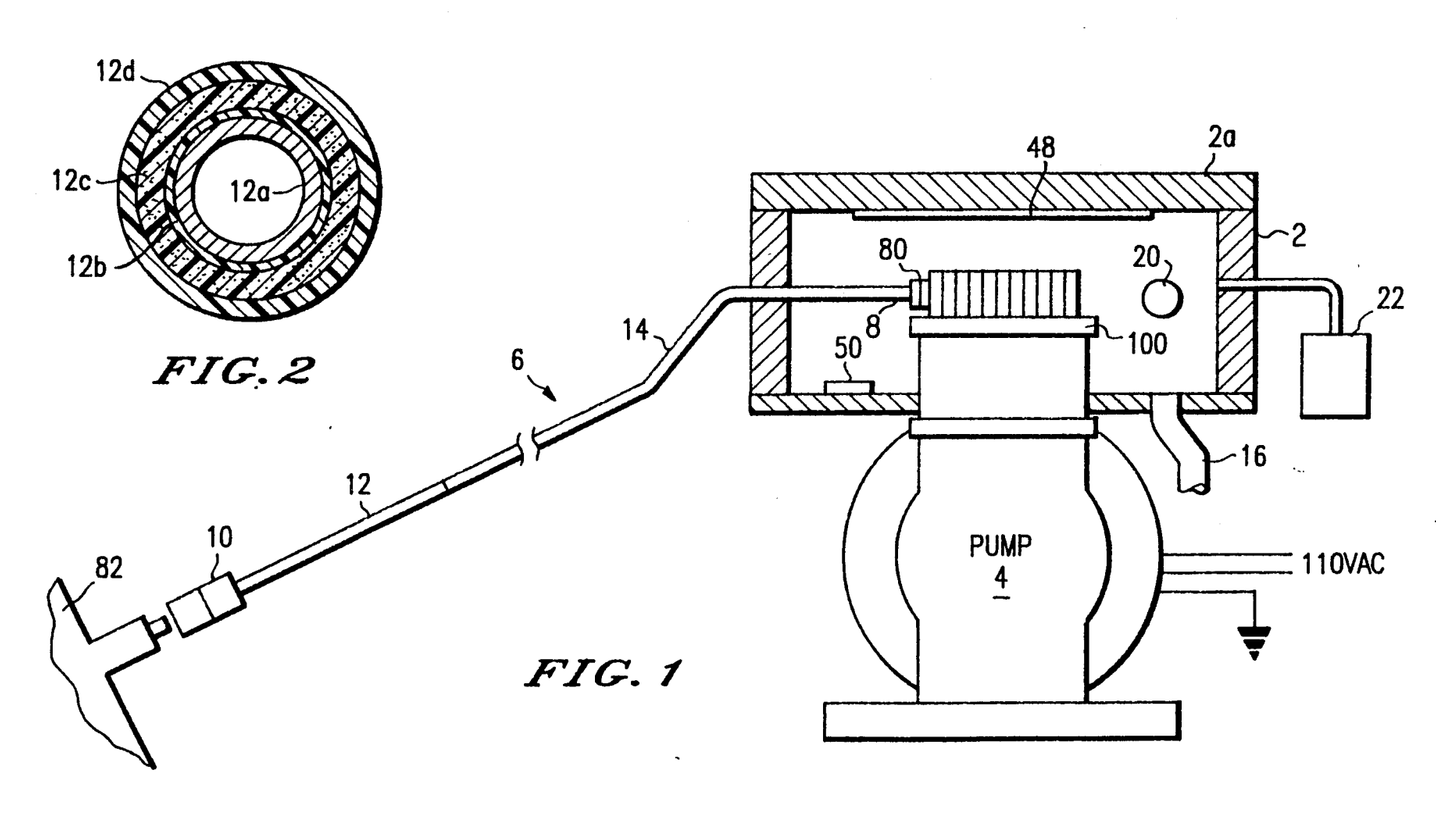
FIG. 1 is a schematic view of the pump, sample chamber and sample conduit of the present invention.
FIG. 2 is a sectional view through the cool down portion of the sample conduit.

Generally, the preferred embodiment carries out a process in which a high temperature sample gas is cooled to a temperature below about 300° F. and is there sampled at positive pressure by use of a thin film polymer type humidity/temperature sensor. This prevents the danger of damage to the sensor while permitting the use of a sensor which does not require oxygen, ice water or cleaning fluids. Referring to FIG. 1, a closed sample chamber 2 is formed from a rigid insulating material, preferably synthetic mica, known by the trade name of "Mycalex". The pump head 100, including the high pressure outlet, of an electrically driven diaphragm pump 4 is fitted in the pump chamber 2, preferably by being fluid tightly mounted thereto in a manner which would be obvious to those skilled in the art. The sample chamber 2 has a sealable opening (not shown) for access to the pump head. For example, the lid 2a of the sample chamber may be removably mounted and positioned by pins extending from the chamber walls and inserted in positioning holes of the lid.

A sample conduit 6 has one end connected to the suction inlet of the pump 4 via a quick release coupling 8 of any well known type, for example the QF-4-B-4PM by NUPRO Company. A fine mesh (40 to 140 micron) stainless steel in line filter 10 is positioned at the inlet end of the conduit 6.

The sample conduit 6 is formed in two parts. A first, cool down, portion 12 is formed at the end of the conduit 6 closest to the filter 10 and the region whose humidity is to be measured. The hot gas loses heat by conduction through the sample conduit 6 and so cools as it approaches the pump 4. The rate of cooling is greatest at the cool down portion 12 of the sample conduit 6, i.e., at that end closest to the filter 10. Nonetheless, the inlet end of the conduit 6 is subjected to high temperatures as high as 600° F., or more. It is therefore necessary to form the cool down portion 12 of a material capable of withstanding high temperatures without damage.

In the preferred embodiment shown in FIG. 2, the cool down portion 12 is formed with a stainless steel inner sleeve 12a, and so is rigid. The stainless steel inner sleeve is capable of withstanding the expected temperatures without damage, but its high conductivity presents the danger of cooling to a temperature where condensation of the sample gas may occur. The cool down portion 12 therefore provides for both heat tracing and insulation for the stainless steel sleeve. For example, the stainless steel sleeve 12a can be covered by a spirally wound heat tracing tape 12b, which is in turn covered with a foam insulation 12c, the entire arrangement being enclosed within a hard insulating casing 12d, such as one formed of polyurethane.

As the high temperature gas from the high temperature region 82 passes through the cool down portion 12, its temperature drops from as high as 600° F., or more, to a temperature near that at which sampling can be performed, i.e., to near 300° F., and preferably to about 400° F. The heat tracing and insulation assure that the temperature of the gas in the cool down portion will not fall to a temperature where condensation becomes a problem.

The remainder of the sample conduit 6 is formed as a flexible portion 14 which is made from a high temperature insulating material, for example nylon fiber reinforced polytetrafluoroethylene (Teflon). At least a portion of the flexible portion 14 is heat traced and further insulated. Moreover, the flexible portion 14 is connected to the pump 4 via quick disconnect 8 and to the cool down portion 12 in an airtight manner.

An exhaust conduit 16 is connected to the bottom of the sample chamber 2 and leads to an atmospheric port.

The relative humidity and temperature of the sample air within the sample chamber are measured by the probe of a solid state thin film type relative humidity/temperature sensor 20 such as the thin film polymer sensor HT-250R manufactured by Rotronic Instrument Corporation of Huntington, NY. The Rotronic sensor can measure relative humidity and temperatures in environments up to 302° F. Additionally, an electronic barometer 22 is mounted to the outside of the sample chamber. It has a port extending into the sample chamber, and so can measure the absolute pressure (barometric pressure plus gauge pressure) within the sample chamber. The barometer 22 is preferably the PX961 by OMEGA Engineering.

Although the relative humidity can be directly measured, it varies with the temperature of the sample, and so is not a good indicator of the absolute moisture content. However, both the dew point (Tdp) and humidity ratio (W) of the sample can be calculated based upon the relative humidity, temperature and, in the case of humidity ratio, absolute pressure, as follows:

Antoine's equation:

$$p^*v = 10^{(A-(B/(Tc+C)))} \qquad 1$$

where:

$p^*v$ is the saturated vapor pressure Tc is the measured temperature in celsius A,B,C are coef. for water that change at 60C and have the values: 8.10765; 1750.286; 235 for Tc<60C 7.96681; 1668.210; 228 for 60C<Tc 150C, $$pv = (hr \times p^*v)/100\% \qquad 2$$

where:

pv is the partial pressure of the vapor whose relative humidity hr is measured, yH20 = pv/Pa    3 where: yH20 is the mole fraction of water, and absolute pressure Pa is measured, $$yH20/(1-yH20) = yH20/yDA \qquad 4$$

where:

yDA is the mole fraction of dry air, Humidity Ratio (W) =

$$(yH20/yDA) \times (18 \text{ lbs H20}/29 \text{ lbs DA}) \qquad 5$$

where:

18 and 29 are the equivalent weights of water and dry air respectively. Units are thus lbs H20/lb DA For dew point (Tdp) calculations:

using eq. 1: $p^*v = 10^{\wedge} (A - (B/(Tc+C)))$
using eq. 2: $pv' = (hr \times p^*v) / 100\%$ where:

pv' denotes partial pressure calculated based on Tc and hr of system by eq. 2 pv = (hr x p* v) / 100% then at dew point hr=100% (by definition). Thus at dew point pv=p*v by eq. 2 and Tdp=((B/(A−log pv'))−C.

The above calculations of humidity ratio and dew point are preferably performed by a programmable computer 24 such as an Opto 22 Model LC 2 computer (FIG. 3) which receives data from the relative humidity/temperature sensor 20 and pressure transmitter 22 via an A/D input/output rack 26 which may be an Opto 22 manufactured I/0 rack. The calculated values for humidity ratio and dew point are sent back to the I/0 rack 26 and supplied, together with the sensed relative humidity, temperature and absolute pressure as analog outputs to a digital process indicator 28 including optical displays, such as DP81-V-206-SCL by OMEGA Engineering. An analog output from the I/O rack 26 can also be delivered to a chart recorded 30 for keeping a written record of the humidity ratio and/or dew point over time.

Figure 3:
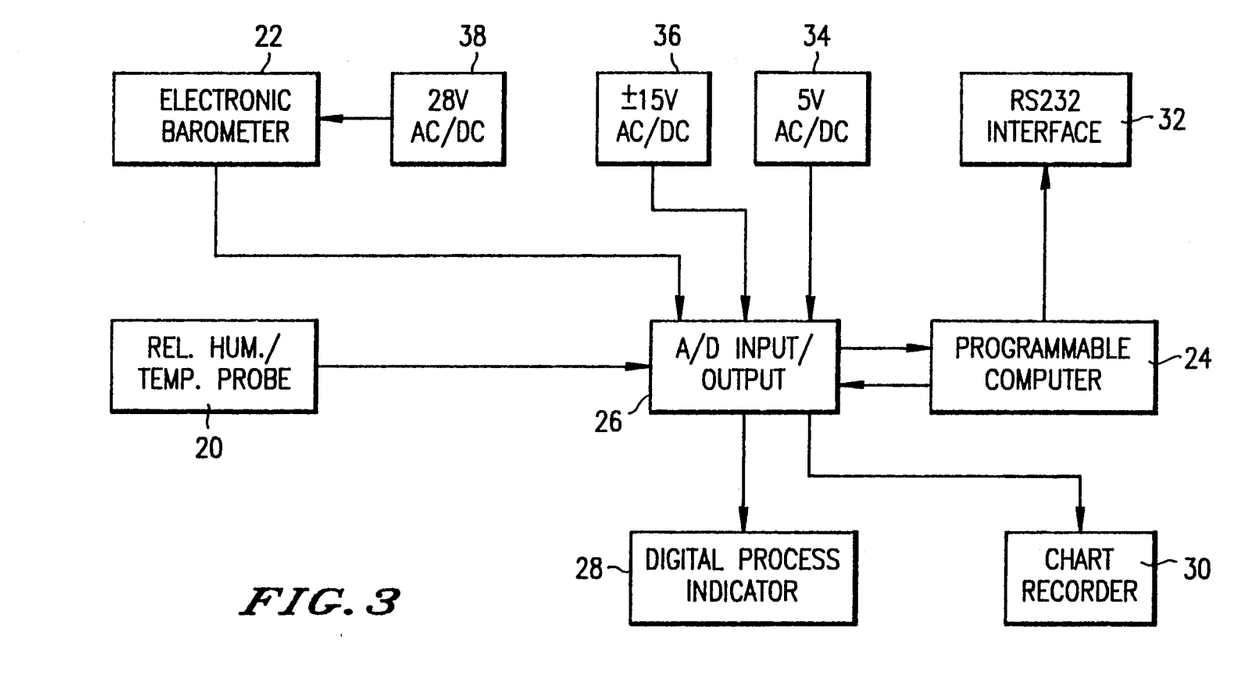
FIG. 3 is a block diagram of the connection of the electronic components for humidity ratio and dew point determination and display.

The computer 24 is also connected to an RS232 interface 32 such as an Opto 22 AC 7 card which permits output to, for example, a general purpose computer programmed to allow the user to watch all five outputs (i.e., measured pressure, temperature and relative humidity, and calculated W and Tdp), log the outputs to disk at specified intervals and have a real time trending displayed. The data can also be stored in a file for ease of use with conventional spread sheet software.

The I/O rack 26 receives both 5 volt DC current and ±15 volt DC current from modules 34 and 36 which convert a 110 volt AC commercially available current. The commercially available current is also converted to a 28 volts DC current by the module 38 and delivered to the electronic barometer 22.

Although the humidity ratio of a hot air sample remains constant at all temperatures, this is only true so long as the air sample at all times remains above its dew point temperature. If the sample falls below the dew point temperature at any time, condensation will occur, affecting the accuracy of the relative humidity readings. These dew points range as high as 210° F. It is therefore important that the sample always be maintained above the dew point temperature, and preferably 10°-20° F. higher. Conversely, the sample must also be maintained below about 300° F. in order to avoid damage to the probe.

Figure 4:
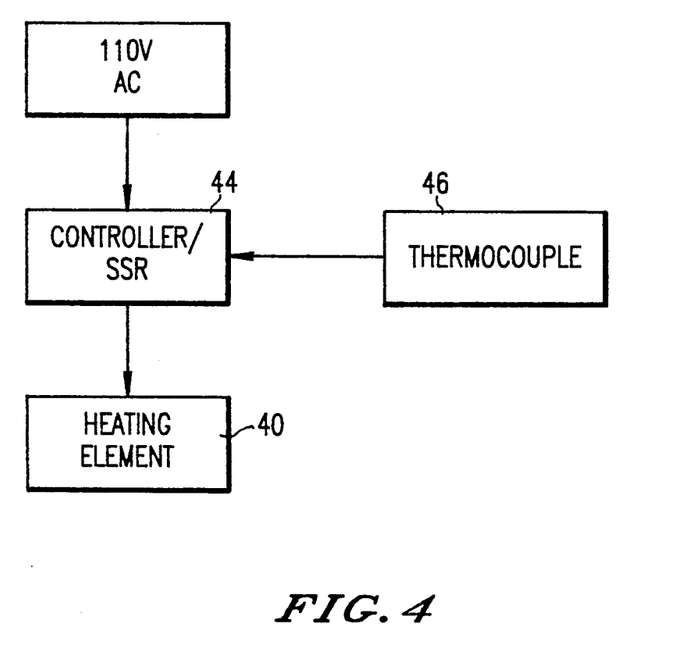
FIG. 4 is a block diagram of the electronic components for the hose temperature control system.
Figure 5:
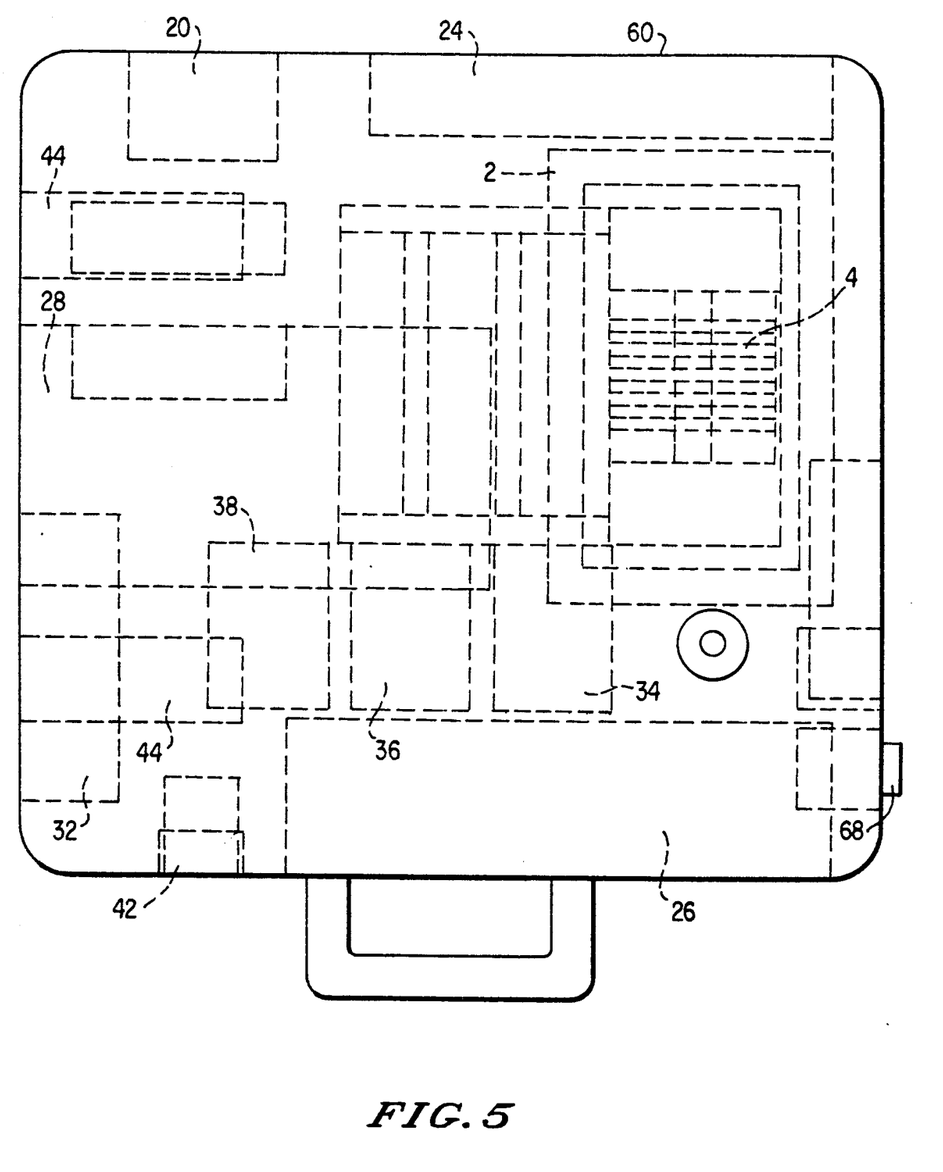
FIG. 5 is a top view of a casing containing the device of the invention.
Figure 6:
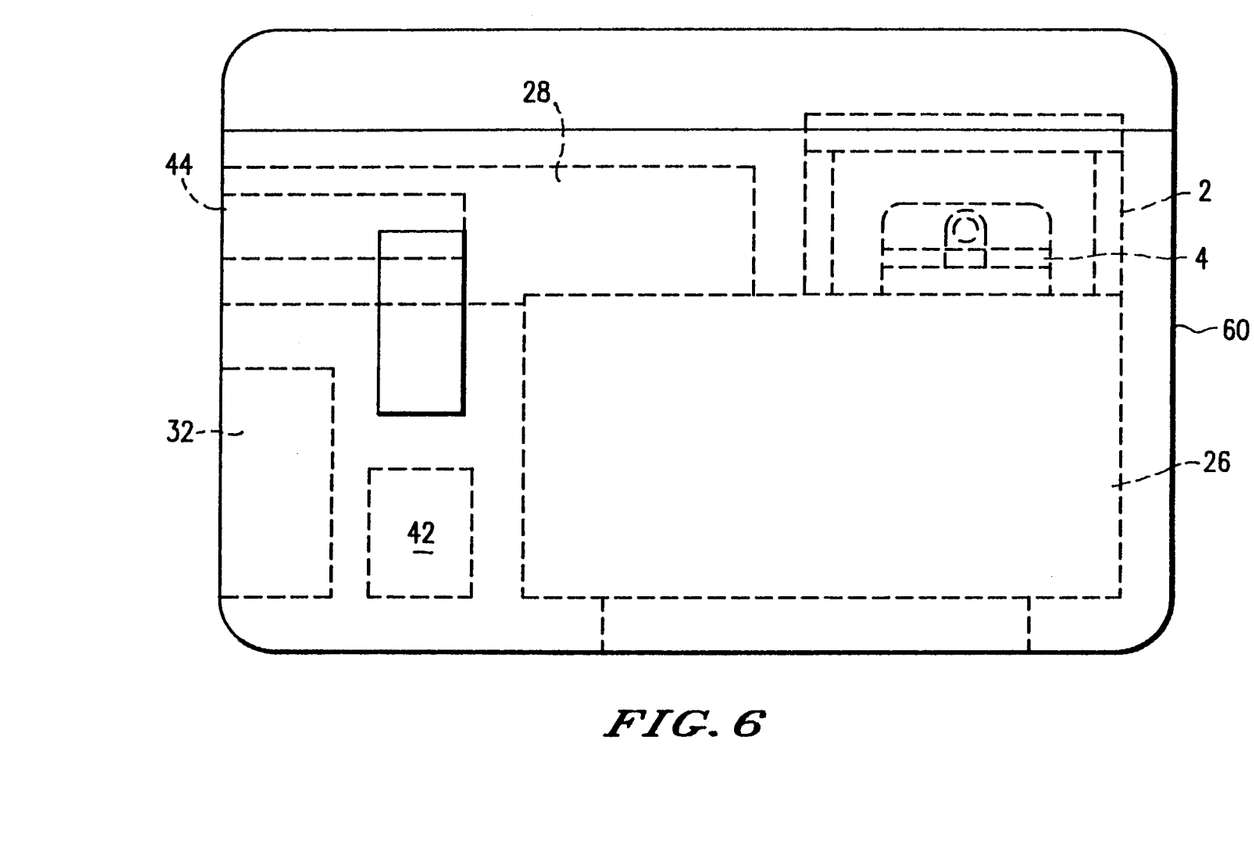
FIG. 6 is a front view of the casing of FIG. 4.
Figure 7:
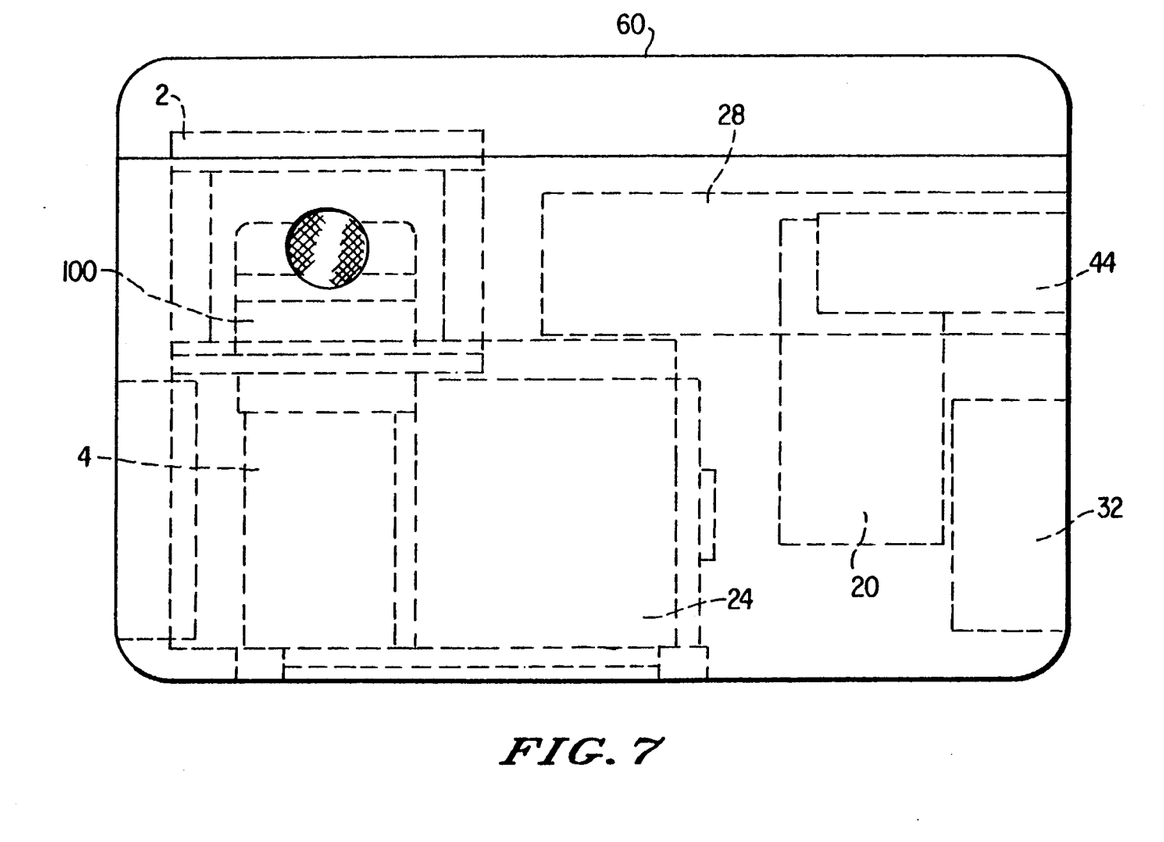
FIG. 7 is a back view of the casing of FIG. 5.
Figure 8:
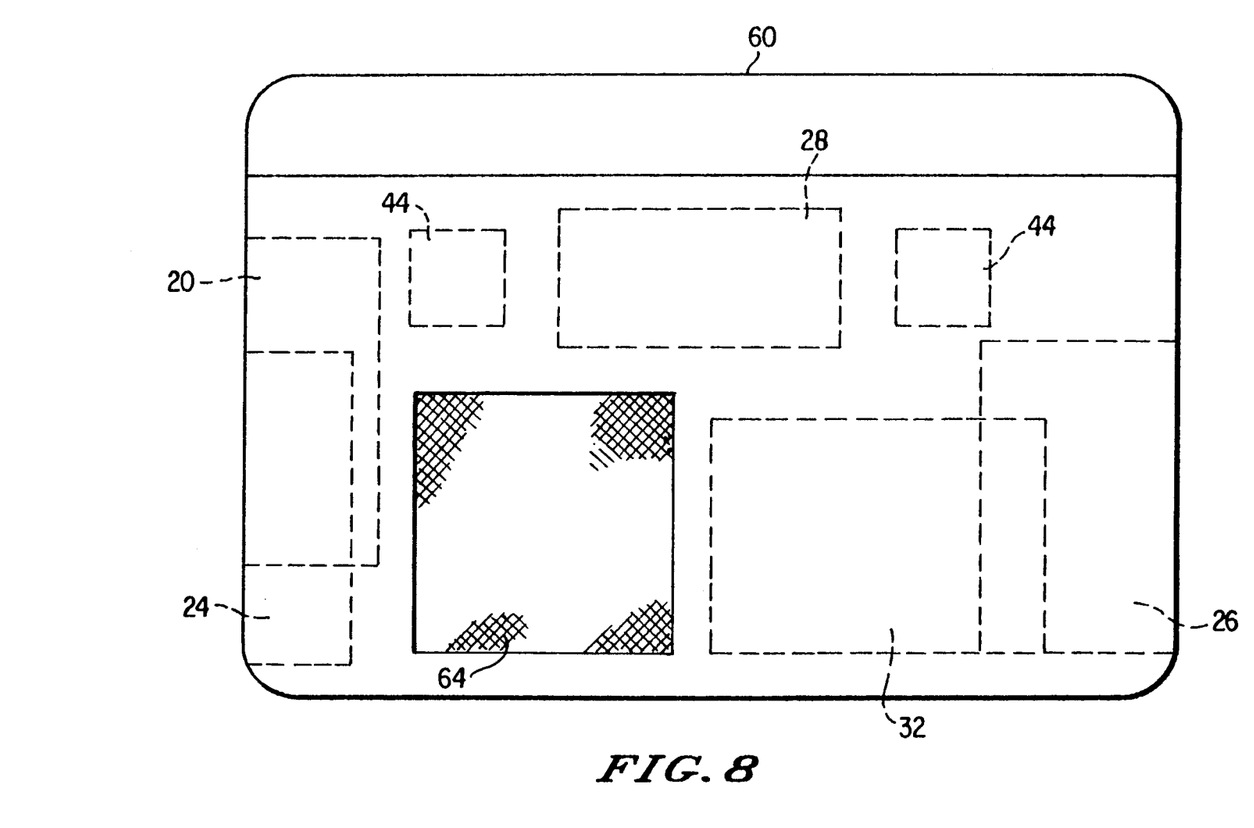
FIGS. 8 and 9 side views of the casing of FIG. 5.
Figure 9:
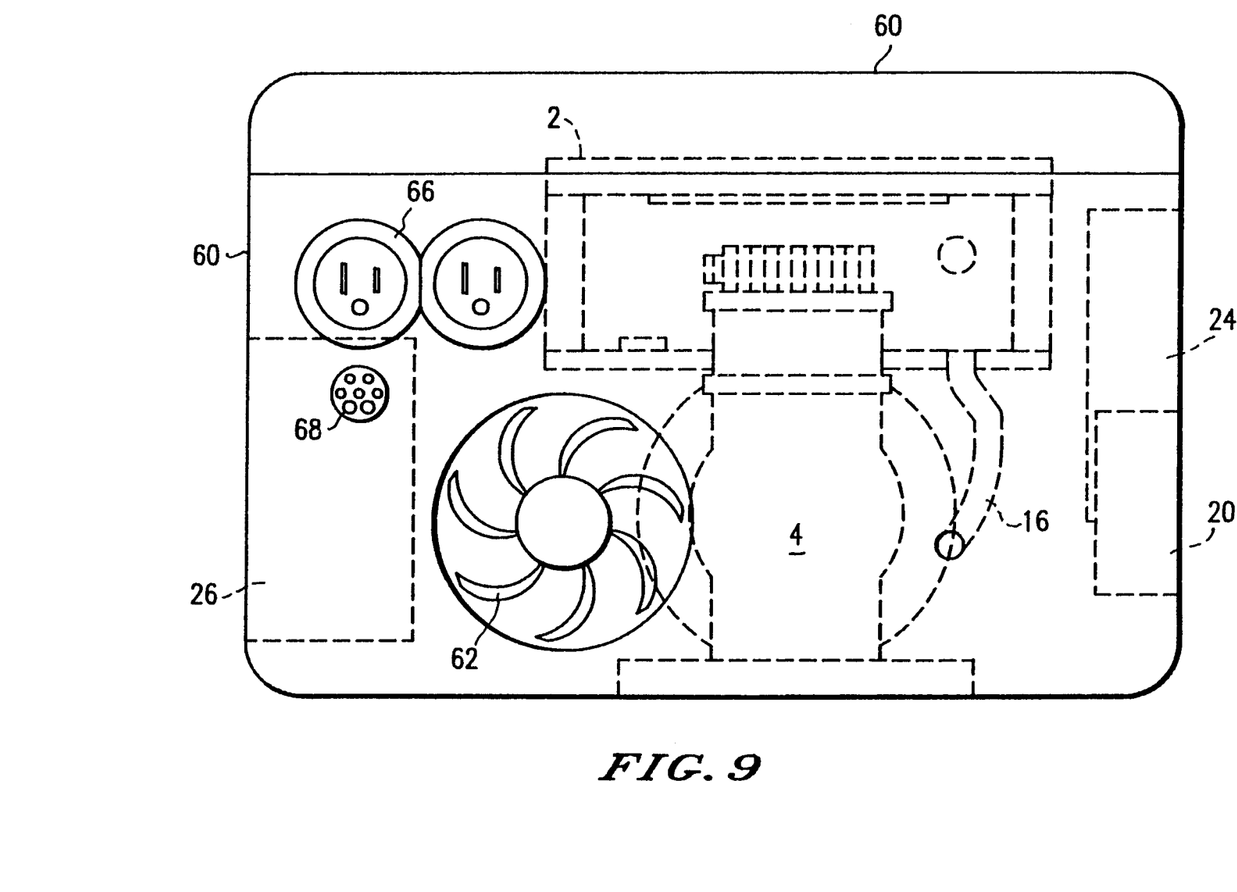

As described above, the temperature of the sample drops in the sample conduit 6. The length of the rigid portion 12 should be selected so that an anticipated sample will be cooled to below the maximum temperature range of the flexible conduit, preferably 300° F.–400° F., at the downstream end of the rigid portion 12. The temperature of the sample at the downstream end of the flexible portion must not be so low that condensation will occur before the sample reaches the sample chamber 2. This cannot be reliably done by the simple expedient of selecting the length of the rigid and flexible portions 12 and 14, since the temperature of the sample which reaches the sample chamber 2 will be affected by other factors, including ambient air temperature, the insulating qualities of the sample conduit 6 and the length of the sample conduit 6. The present invention therefore provides a thermostatically controlled heater in the sample conduit 6. For example, the sample conduit 6 is heat traced with a heater wire as a heating element 40 (FIG. 4). The current to the heating element 40 is delivered through a solid state relay (SSR) 42 whose operation is controlled by a solid state controller 44, such as CN9111 by OMEGA Engineering. The controller 44 is in turn thermostatically responsive to signals from a K type thermocouple 46 cemented to the interior of the portion 14 of the sample conduit 6 at the downstream end thereof. The controller 44 has PID control algorithms for thermostatically maintaining the temperature of the sample at the desired set point, for example above the dew point temperature but below 300° F.

Similar considerations hold true within the sample chamber itself. For this purpose, heating mats 48 (only one is shown in FIG. 1, although 3 are preferred) are mounted within the sample chamber and thermostatically controlled by a controller similar to controller 44, but responsive to a thermocouple 50 cemented to the bottom of the sample chamber.

An important feature of the present invention is that the sample chamber 2 is positively pressurized by the pump 4. This eliminates the danger of air leaks into the sample chamber which would produce false humidity readings. Any air leaks within the sample chamber would leak air out, and so would not affect the humidity readings.

Although the sample conduit 6 is at negative pressure, air leaks from the sample conduit can be prevented by a tight connection between the sample conduit 6 and the region 82 whose humidity is to be measured. This connection can be made by a releasable connector such as a nut and ferrule. Quick release connectors are to be avoided at this location because they have a tendency to leak.

On the other hand, a quick release connector 8 is used at the connection between the sample conduit 6 and the pump head 100. Since this connection is within the sample chamber, which is at positive pressure, any leakage will be of gas into the pump head and that leakage will be of sample gas, so that the accuracy of humidity readings will not be affected.

Another important feature of the invention is the use of a Mycalex sample chamber. Mycalex has the dual benefit of being both easy to machine and heat insulating. Machinability is important because the walls must be drilled and tapped for assembly, and holes must be drilled and tapped in the walls for the sensors 20 and 22. Heat insulation is important because heat losses through the wall of the sample chamber could produce a temperature gradient near the walls. Since the measured relative humidity is temperature dependent, false temperature readings will result in false humidity ratio readings. Good insulation characteristics for the walls of the sample chamber are also important to avoid the formation of localized cold regions in which condensation can occur.

Low heat loss through the walls of the sample chamber is also important in minimizing the frequency of the heat up-cool down cycles of the temperature controller for the heating mats 48. The sensor 20 responds more rapidly to changes in relative humidity than it does to changes in temperature, which means that the computer 24 will calculate false humidity ratio values until both the relative humidity and temperature stabilize. High insulation values for the sample chamber walls will minimize temperature fluctuations, and so will minimize errors due to nonstable temperatures.

The humidity determining device of the invention is preferably contained within a case, and so is portable. Top, front, back and side views of the case, showing the components contained therein in shadow, are shown in FIGS. 5-9, respectively. The case 60 can be hinged and releasably latched for access to the components therein. The case has additional components necessitated by the portable nature of the device. For example, a fan 62 having a filter (not shown) circulates air through the case and vents the same through vent 64 in order to prevent heat build-up within the case which could damage the electrical components of the I/O rack, computer, etc. Electrical plugs 66 provide connections for standard 110 volt AC current which directly powers the heating elements 40 or 48 for the hose and sample chamber, and which power the low voltage components via the modules 34–38. An amphenol military type connector 68 mounted on the casing provides electrical connection for the conduit heating elements 40 and K thermocouple 46.

In use, the case is opened, the sample conduit 6 is removed from the casing and the heating elements thereof plugged into the connector 68.

After opening the mycalex sample chamber, the quick release connector 8 is connected to a mating connection 80 at the pump head, then the sample chamber is sealed closed. Standard, commercially available electrical power is then supplied to the device via plug 66. After power to the device has been turned on, the controllers 44 for heating elements 40 and 48 are adjusted to their set point temperatures. Once the temperatures are stable, the inlet end of sample conduit 6 is connected in order to draw hot air from the region 82 to be sampled, through the sample conduit 6, into the sample chamber 2, and out through the exhaust conduit 16 which exhausts outside of the case 60. The process indicator 28 is then monitored until the detected temperature, relative humidity and pressure stabilize, at which point an accurate reading of the humidity ratio and dew point of the sample can be continuously determined.

It should be noted that the accuracy of the preferred humidity/temperature sensor 20 is at a maximum for relative humidities above 10%. The controllers 44 should therefore be set so that the relative humidity is always maintained above 10%. For example, if the dew point is 70° F. and the controllers' set point is set at 160° F., then the sample relative humidity will be approximately 8%. The set point should therefore be reduced to a level in which the relative humidity is greater than 10%, but less than 100%. For example, in the above example the lower set point could be 100° F., at which temperature the relative humidity is approximately 40%.

Obviously, numerous modifications and variations of the present invention are possible in light of the above teachings. It is therefore to be understood that within the scope of the appended claims, the invention may be practiced otherwise than as specifically described herein.

WHAT IS NEW AND DESIRED TO BE SECURED BY LETTERS PATENT OF THE UNITED STATES IS:

1. A high temperature humidity determining device comprising:
   an insulated sample chamber;
   means for inducing a heated air sample from a region whose humidity is to be measured to flow into said insulated sample chamber, said inducing means including a sample conduit connected to said region and having at least a cool down portion, whereby the heated air sample is cooled before reaching said insulated sample chamber;
   heating means for controlling the temperature of said heated air sample such that said heated air sample always remains above the dew point thereof in said insulated sample chamber and said inducing means;
   sensing means for sensing at least the temperature and relative humidity of the air sample in said insulated sample chamber; and
   means for determining a humidity parameter of the air sample based upon at least the sensed temperature and relative humidity.

2. The device of claim 1 wherein said inducing means includes a pump connected between said sample conduit and said insulated sample chamber, whereby said insulated sample chamber is positively pressurized by said air sample pumped by said pump.

3. The device of claim 2 wherein said sample conduit includes a flexible portion connected between a rigid cool down portion and said pump.

4. The device of claim 3 wherein said heating means comprises heating elements in said conduit, a conduit temperature sensor and an automatic control device comprising means for controlling actuation of said heating elements based upon the sensed temperature from said conduit temperature sensor. sensor.

5. The device of claim 4 wherein said heating means further comprises heating elements in said heating chamber and a sample chamber temperature sensor, and wherein said automatic control device further comprises means for controlling actuation of said heating elements in said insulated sample chamber based upon the sensed temperature from said sample chamber temperature sensor.

6. The device of claim 5 wherein said automatic control device comprises means having PID control algorithms about a set point for the air sample temperature.

7. The device of claim 2 including an air exhaust in said insulated sample chamber.

8. The device of claim 1 wherein said heating means comprises heating elements in said heating chamber and a sample chamber temperature sensor, and wherein said automatic control device comprises means for controlling actuation of said heating elements in said insulated sample chamber based upon the sensed temperature from said sample chamber temperature sensor.

9. The device of claim 1 wherein said sensing means further comprise means for sensing the absolute air pressure in said insulated sample chamber, and wherein said determining means comprise means for determining the humidity parameter of the air sample based upon the sensed temperature, relative humidity and absolute pressure.

10. The device of claim 9 wherein said humidity parameter is one of the humidity ratio and the dew point temperature of the air sample and wherein said determining means comprise a digital processor programmed to calculate the humidity ratio of the sample air.

11. The device of claim 10 including humidity parameter display means connected to said digital processor for displaying at least one of the calculated humidity ratio and the calculated dew point temperature.

12. The device of claim 1 wherein said insulated sample chamber is formed from Mycalex.

13. The device of claim 1 wherein said relative humidity and temperature sensors are together comprised by a thin film polymer type humidity/temperature sensor.

14. The device of claim 1 including an air tight quick disconnect connector between said sample conduit and said sampling pump.

15. The device of claim 1 including a case containing at least said insulated chamber, said inducing means, said heating means and said determining means, whereby said humidity determining device is portable.

16. A process for determining a humidity parameter of a heated air sample having a temperature greater than 300° F. and a dew point temperature as high as 210° F., comprising the steps of:
   cooling the air sample to a temperature range above the dew point temperature of the sample and below about 300° F.;
   maintaining the air sample temperature in said range;
   continuously flowing the air sample into an insulated sample chamber at positive pressure;
   sensing at least the temperature and relative humidity of the air sample maintained in said range by use of a thin film polymer type humidity/temperature sensor; and
   calculating the humidity parameter based upon at least the sensed temperature and relative humidity.

17. The process of claim 16 including the steps of sensing the absolute pressure of the air sample and calculating the humidity parameter based upon the sensed temperature, relative humidity and absolute pressure.

18. The process of claim 17 wherein said humidity parameter is one of the humidity ratio and the dew point temperature of the air sample.

19. The process of claim 16 wherein said temperature range is selected such that the sensed relative humidity is greater than 10%.

20. The process of claim 16 including the step of displaying the calculated humidity parameter.

21. The process of claim 16 including the step of continuously flowing the air sample into a sample chamber at a controlled flow rate.

22. The process of claim 16, wherein said heated air sample has a temperature of at least 600° F.

23. An apparatus for determining a humidity parameter of a heated air sample having a temperature greater than 300° F., comprising:
- means for cooling the air sample to a temperature range above the dew point temperature of the sample and below about 300° F.;
- means for maintaining the air sample temperature in said range;
- means for continuously flowing the air sample into an insulated sample chamber at positive pressure;
- means for sensing at least the temperature and relative humidity of the air sample maintained in said range by use of a thin film polymer type humidity/temperature sensor; and
- means for calculating the humidity parameter based upon at least the sensed temperature and relative humidity.

24. A portable and self-contained, high temperature humidity determining device comprising:
- a case;
- an insulated sample chamber having an exhaust and being fixed in said case;
- a diaphragm type air pump fixed in said case and operatively connected to said sample chamber for pumping air into said sample chamber, whereby a flow of heated sample air in said sample chamber is positively pressurized;
- thermostatically controlled heating elements in said sample chamber for maintaining air in said sample chamber at a predetermined temperature;
- an airtight sample conduit having one end connected via a quick disconnect to said pump and another end connectable to a region whose humidity is to be measured, whereby heated air from said region is pumped to said sample chamber, said another end of said sample conduit comprising a rigid cool down portion comprising a high heat conductive material, heat trace means, and insulation whereby a temperature of air from said region may drop to near said predetermined temperature, said another end of said sample conduit comprising a flexible portion, said sample conduit being thermostatically heated whereby the air may be maintained at near said predetermined temperature;
- thin film polymer type relative humidity and temperature sensors in said sample chamber;
- an absolute pressure sensor mounted to said chamber;
- a programmable computer fixed in said case and being operatively connected to said sensors, said computer including means for calculating at least the humidity ratio and the dew point of the air in said sample chamber based on signals from said sensors; and
- electronic display means in said case and operatively connected to said computer for displaying at least said calculated dew point and humidity ratio.

25. The device of claim 24, wherein said sample chamber is formed of Mycalex.

* * * * *